United States Patent [19]

Cunningham et al.

[11] Patent Number: 4,940,788
[45] Date of Patent: Jul. 10, 1990

[54] PROCESS FOR PREPARING AZETIDINONES

[75] Inventors: Ian M. Cunningham; David W. Heaton, both of Congleton, United Kingdom

[73] Assignee: Imperial Chemical Industries PLC, London, England

[21] Appl. No.: 145,818

[22] Filed: Jan. 19, 1988

[30] Foreign Application Priority Data

Jan. 30, 1987 [GB] United Kingdom ............... 8702139

[51] Int. Cl.$^5$ ............... C07D 303/04; C07D 205/02
[52] U.S. Cl. ........................... 540/200; 540/310; 540/350; 549/512
[58] Field of Search ............... 549/512; 540/310, 200, 540/350

[56] References Cited

FOREIGN PATENT DOCUMENTS 181831  5/1986  European Pat. Off. .
221846  5/1987  European Pat. Off. .

OTHER PUBLICATIONS

Tetrahedron Letters, vol. 24, No. 10, pp. 1037–1040 (1983).
Journal of the American Chemical Society, Vol. 107, pp. 1438–1439 (1985).
Bulletin of the Chemical Society of Japan, vol. 58, pp. 3264–3270 (1985).
Tetrahedron Letters, vol. 39, No. 14, pp. 2399–2407 (1983).

Primary Examiner—Nicholas S. Rizzo
Attorney, Agent, or Firm—Cushman, Darby & Cushman

[57] ABSTRACT

A process for preparing azetidinones of the formula:

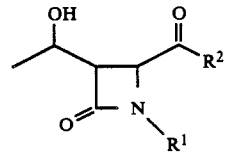

wherein $R^1$ is an amino-protecting group and $R^2$ is alkyl or aryl, which comprises reacting compounds of the formulae (VIII) and (IX)

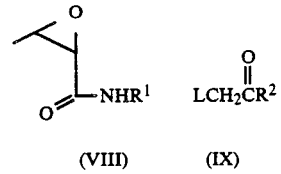

(VIII)       (IX)

wherein L is a leaving group. The product azetidinones are intermediates in the preparation of penem and carbapenem antibiotics.

5 Claims, No Drawings

PROCESS FOR PREPARING AZETIDINONES

The present invention relates to a process for preparing β-lactams and in particular to a process for preparing intermediates useful in the synthesis of carbapenem and penem antibiotics.

In the past few years many groups of research workers have investigated the synthesis of carbapenems, penems, monobactams and penicillin and cephalosporin analogues. These syntheses have depended to a large extent on the ability to control stereochemistry and on the ability to prepare key intermediates conveniently and in good yields. One such class of azetidinone intermediates is that of the formula (I):

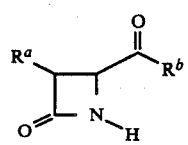
(I)

wherein $R^a$ and $R^b$ represent a variety of organic groups. The group $R^bCO-$ can be converted into a variety of groups at the 4-position of the azetidinone ring; typically such groups are subsequently cyclized on to the nitrogen atom or on to a suitable substituent of said nitrogen atom to form carbapenems and penems. For example, as described in EP-A No. 181831, a compound of the formula (II) is subjected to a Baeyer-Villiger reaction with peracid to form a compound of the formula (III) which is subsequently converted to a penem of formula (IV) via displacement of the PhCOO—substituent, elaboration of the N-substituent, cyclization and deprotection.

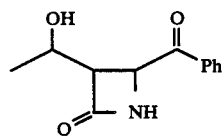
(II)

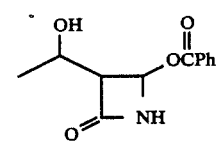
(III)

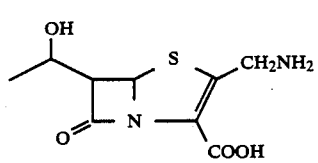
(IV)

The compounds of the formula (I) can be prepared in a variety of ways, for example see the disclosures of Yanagisawa et al., Tetrahedron Letters 1037 (1983), Shiozaki et al., Tetrahedron 2399 (1983), Hanessian et al., J.A.C.S. (107) 1438 (1985) and Maruyama et al., Bull. Chem. Soc. Japan (58) 3264 (1985). In general these disclosures describe inter alia the preparation of a compound of the formula (I) via the intermediacy of compounds of the formulae (V) and/or (VI):

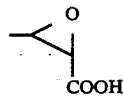
(V)

(VI)

wherein $R^1$ is an amino-protecting group.

The present invention provides a process that avoids the use of intermediates of these types and therefore avoids any difficulties associated with processes involving such intermediates.

Accordingly the present invention provides a process for preparing a compound of the formula (VII)

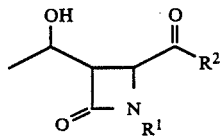
(VII)

wherein $R^1$ is an amino-protecting group and $R^2$ is an alkyl or aryl group, which process comprises reacting a compound of the formula (VIII) with a compound of the formula (IX)

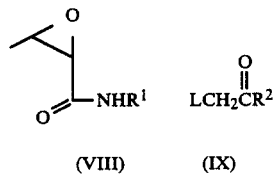

(VIII)   (IX)

wherein L is a leaving group.

The reaction is typically performed in the presence of a base for example sodium hydride. Typically the reaction is performed at any non-extreme temperature, for example between −70° C. and 50° C., most conveniently at room temperature. Generally the reaction is performed in a solvent for example toluene, tetrahydrofuran, dioxan, dimethoxyethane and methyl t-butyl ether.

The reaction proceeds via the compound of the formula (X)

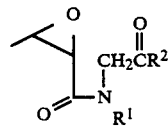
(X)

wherein $R^1$ and $R^2$ are as hereinbefore defined. The compound of the formula (X) can be isolated if desired. The intermediate of the formula (X) can be converted completely to the compound of formula (I) by further treatment with base, e.g. lithium hydroxide, with stirring, for example at room temperature.

Examples of meanings for the amino protecting group $R^1$ include aryl (e.g. phenyl and substituted phenyl, e.g. p-methoxy-phenyl); aryl lower alkyl (e.g. benzyl and substituted benzyl, e.g. p-methoxybenzyl and 2,4-dimethoxybenzyl, and triphenylmethyl); di-p-anisylmethyl and furylmethyl, acyl (e.g. lower alkoxycarbonyl and aryl lower alkoxycarbonyl e.g. t-butoxycarbonyl and benzyloxycarbonyl); and tri lower alkylsilyl (e.g. trimethylsilyl and t-butyl-dimethylsilyl).

Examples of meanings for the leaving group L include halogen, in particular bromine.

Examples of meanings for the group $R^2$ include (1-6-C)alkyl, e.g. methyl, ethyl, n-propyl, isopropyl and butyl, in particular t-butyl, and phenyl optionally substituted, e.g. by (1-6C)alkyl, (1-6C)alkoxy, halogen or (2-6C)alkoxycarbonyl.

The compounds of the formula (VIII) are known from, or preparable by, general chemical methods for example see Yanagisawa et al., Tet.Lett. 1017 (1983).

The invention is illustrated by the following Examples, in which the following abbreviations are used:
HPLC = high preformance liquid chromatography
NMR = nuclear magnetic resonance spectroscopy
THF = tetrahydrofuran
FAB = fast atom bombardment
40–60 petrol = petroleum ether boiling at 40°–60°.

The NMR spectra are taken at 200 MHz and are quoted in terms of delta values in parts per million (ppm). In the quotation of NMR data standard abbreviations are used s = singlet, d = doublet, t = triplet, q = quartet, m = multiplet and br = broad, J = coupling constant.

EXAMPLE 1

(3S, 4S, 1'R) N-p-methoxyphenyl-3-(1'-hydroxyethyl)-4-benzoylazetidin-2-one

To a solution of 2R,3R-2,3-epoxybutyric acid-p-methoxyphenylamide (207 mg) in dry THF (4.0 ml) under argon was added 60% sodium hydride dispersion (40 mg). The mixture was stirred at ambient temperature for 10 mins. A solution of phenacyl bromide in dry THF (3.0 ml) was then added rapidly to the stirred reaction mixture. The reaction mixture was stirred for a further 1.5 hours at ambient temperature and then diluted with ether (30 ml) and poured on to a stirred mixture of 0.5M HCl (30 ml) and ether (30 ml). The layers were separated and the organic extract washed with water (40 ml) and saturated aqueous sodium chloride (30 ml). The organic layer was dried over anhydrous sodium sulphate, filtered and evaporated to dryness. The residue was purified by flash chromatography on silica (Kieselgel 60) using stepwise gradient elution with ethyl acetate/dichloromethane (1:9 increasing to 1:1 ethyl acetate/dichloromethane). The appropriate fractions were evaporated to dryness to give a residue which was crystallised from dichloromethane/40αpetrol to give a solid (57.0 mg) which was a mixture of (3S,4S,1'R) N-p-methoxyphenyl-3-(1'-hydroxyethyl)-4-benzoylazetidin-2-one (93%) and (3S,4R,1'R) N-p-methoxyphenyl-3-(1'-hydroxyethyl)-4-benzoylazetidin-2-one (7%).

The 3S,4S,1'R (trans) isomer had the following NMR in CDCl$_3$: 1.35 (d, 3H), 3.23 (dd, 1H), 3.75 (s, 3H), 4.37 (m, 1H), 5.53 (d, J=2.0 Hz,·1H), 6.83 (d, 2H), 7.22 (d, 2H), 7.6 (m, 3H), 8.22 (m, 2H).

Mass Spectrum M+H (FAB)=326.

The 3S,4R,1'R (cis) isomer had the following NMR in CDCl$_3$: 1.55 (d, 3H), 3.65 (s, 3H), 4.95 (m, 1H), 5.62 (d, J=5.0 Hz, 1H), 6.47 (d, 2H), 6.74 (d, 2H), 7.22 (m, 3H), 8.08 (m, 2H).

EXAMPLE 2

(3S,4S,1'R)N-p-methoxyphenyl-3-(1'-hydroxyethyl)-4-pivaloyl-azetidin-2-one

To a solution of 2R,3R-2,3-epoxybutyric acid-p-methoxyphenylamide (414 mg) in dry THF (8.0 ml) under argon was added 60% sodium hydride dispersion (80 mg). The mixture was stirred at ambient temperature for 10 minutes. A solution of 1-bromopinacolone (0.394 g) in dry THF (4.0 ml) was then added rapidly to the stirred reaction mixture. The reaction was stirred for a further 16 hours at ambient temperature and then diluted with ether (50 ml) and water (30 ml) and the layers partitioned. The layers were separated and the organic extract washed with water (40 ml) and saturated aqueous sodium chloride (30 ml). The organic layer was dried over anhydrous sodium sulphate, filtered and evaporated to dryness. The residue was purified by flash chromatography on silica (Kieselgel 60) using a stepwise gradient of ethyl acetate/dichloromethane (1:7 increasing to 100% ethyl acetate) to give two fractions, A (170 mg) and B (320 mg). Fraction A was crystallised from ether/40–60 petrol to give (3S,4S,1'R)N-p-methoxyphenyl-3-(1'-hydroxy ethyl)-4-pivalolylazetidin-2-one (52 mg) m.p. 82°–84° C.

The compound had the following NMR in CDCl$_3$: 1.32 (s, 9H), 1.46 (d, 3H), 3.06 (dd, 1H), 3.77 (s, 3H), 4.27 (m, 1H), 4.98 (d, J=2.0 Hz, 1H), 6.86 (d, 2H), 7.17 (d, 2H).

Mass spectrum M+H (FAB)=306.

Fraction B was a mixture of the aforementioned azetidin-2-one and (2R,3R)-2,3-epoxybutyric acid N-p-methyl-phenyl N-(3,3-dimethylbutan-2-one)amide, NMR (CDCl$_3$): 1.28 (s, 9H), 1.45 (d, 3H), 3.05 (m, 1H), 3.32 (d, 1H), 3.85 (s, 3H), 4.34 (d, 1H), 4.85 (d, 1H), 6.9 (d, 2H), 7.3 (d, 1H).

Fraction B was converted completely to the aformentioned azetidinone-2-one in the followng manner. Fraction B (304 mg) was dissolved in THF (3.0 ml) and water (1.0 ml) and LiOH.H$_2$O (42 mg) added and the mixture stirred at ambient temperature for 20 hours. The reaction mixture was then diluted with ether (50 ml) and water (30 ml) and partitioned. The layers were separated and the organic layer washed with water (30 ml) and saturated sodium chloride (30 ml). The organic layer was dried with anhydrous sodium sulphate, filtered and evaporated to dryness. The residue was purified by flash chromatography using a stepwise gradient elution with ethyl acetate/dichloromethane (1:6 increasing to 1:3.3). The appropriate fractions were evaporated to dryness and the residue was crystallised from ether/40–60 petrol to give the product (59 mg) mp 83.5°–84.5° C. which was identical to the aforementioned azetidin-2-one.

We claim:
1. A process for preparing a compound of the formula (VII):

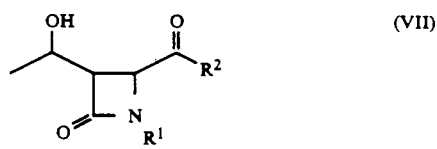

(VII)

wherein $R^1$ is an amino-protecting group and $R^2$ is an alkyl or phenyl optionally substituted by C$_{1-6}$ alkyl, $C_{1-6}$ alkoxy, halogen or $C_{2-6}$ alkoxycarbonyl, which process consists essentially of reacting a compound of the formula (VIII) with a compound of the formula (IX)

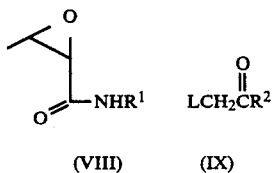

(VIII)   (IX)

wherein L is a halogen group under conditions such that a compound of formula (X) is formed; and

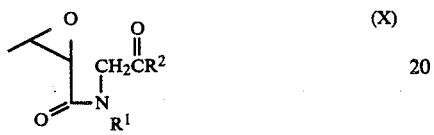

processing said compound of formula (X) under conditions such that said compound of formula (VII) is formed.

2. A process according to claim 1 wherein $R^2$ is (1-6-C)alkyl.

3. A process according to claim 2 wherein $R^2$ is phenyl.

4. A process according to claim 1 wherein $R^1$ is p-methoxyphenyl.

5. A process for preparing a compound of the formula (X):

wherein $R^1$ is an amino-protecting group and $R^2$ is an alkyl or phenyl optionally substituted by $C_{1-6}$ alkyl, $C_{1-6}$ alkoxy, halogen or $C_{2-6}$ alkoxycarbonyl, which process consists essentially of reacting a compound of the formula (VIII)

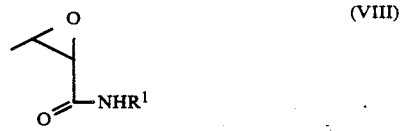

wherein $R^1$ is as defined above with a compound of the formula (IX)

$$LCH_2CR^2 \quad (IX)$$
(with C=O)

wherein $R^2$ is as defined above and L is a halogen group, under conditions such that said compound of formula (X) is formed.

* * * * *